United States Patent [19]

Gilbert

[11] 4,003,953

[45] Jan. 18, 1977

[54] PURIFICATION OF TNT WITH MAGNESIUM SULFITE-BISULFITE MIXTURES

[75] Inventor: Everett E. Gilbert, Morristown, N.J.

[73] Assignee: The United States of America as represented by the Secretary of the Army, Washington, D.C.

[22] Filed: Feb. 23, 1976

[21] Appl. No.: 660,073

[52] U.S. Cl. .................................. 260/645; 260/701
[51] Int. Cl.$^2$ ......................................... C07C 79/10
[58] Field of Search ........................... 260/645, 701

[56] References Cited

UNITED STATES PATENTS 3,956,409   5/1976   Gilbert .............................. 260/645

OTHER PUBLICATIONS

Urbanski, Chemistry and Technology of Explosives, vol. I, The MacMillan Company, New York, 1964, pp. 308 and 332 to 335.

Primary Examiner—Leland A. Sebastian
Attorney, Agent, or Firm—Nathan Edelberg; A. Victor Erkkila

[57]  ABSTRACT

Crude TNT is purified by heating with an aqueous mixture of magnesium sulfite and magnesium bisulfite, whereby TNT is recovered in high yield and purity. The spent aqueous solution can be furnaced to recover magnesium oxide, which can be recycled to the process.

7 Claims, No Drawings

PURIFICATION OF TNT WITH MAGNESIUM SULFITE-BISULFITE MIXTURES

GOVERNMENTAL INTEREST

The invention described herein may be manufactured, used and licensed by or for the Government for governmental purposes without the payment to me of any royalties thereon.

BACKGROUND OF THE INVENTION

TNT (2,4,6-trinitrotoluene, also called αTNT), as conventionally manufactured by nitration processes from toluene and mixed acid as starting materials, contains significant proportions (usually about 4%) of undesired, unsymmetrical isomers. The standard industrial procedure for removing these isomeric impurities is to treat the crude TNT with aqueous sodium sulfite ("sellite"), which reacts with the reactive nitro groups in the meta or 3-position and produces a waste sellite solution containing a mixture of sodium 2,4-dinitrotoluene-3-and-5-sulfonates. The aqueous solution of these sulfonates, commonly referred to as "red water" or "spent sellite," constitutes a pollution and disposal problem. According to current practice, the red water is donated to paper companies, which furnace the material to recover the crude sodium salts (essentially sodium sulfate) for use in their operations. However, such procedure pollutes the atmosphere so that there is doubt as to how long the practice will be permitted to continue.

As far as I am aware, no other sulfite has been proposed for purifying TNT aside from the use of ammonium sulfite recently utilized for such purpose, which is the subject of my copending U.S. application Ser. No. 585,735 for "Process For Purifying TNT," filed June 10, 1975.

Magnesium sulfite has long been employed for the treatment of wood pulp in the manufacture of paper. More recently magnesium oxide has been utilized for the removal of sulfur dioxide from combustion gases (International Journal of Sulfur Chemistry, B, Vol. 7, No. 1, 60 (1972)). In both cases the resulting magnesium salts are converted back to magnesium oxide by heating. The magnesium oxide thus obtained is recycled to the process, which in the case of the pulping process involves reconversion to magnesium sulfite by reaction with sulfur dioxide.

SUMMARY AND DETAILED DESCRIPTION OF THE INVENTION

An object of the present invention is to provide a novel process for purifying crude TNT, whereby a purified TNT product of high purity can be obtained in excellent yield.

Another object is to provide a process for purifying TNT, whereby the pollution problems associated with the purification of TNT can be reduced or substantially eliminated.

Other objects will become apparent as the invention is further described.

According to the present invention the foregoing and other objects can be achieved by reacting the crude TNT with an aqueous mixture of magnesium sulfite and magnesium bisulfite. The spent sulfite liquor can be furnaced directly to recover the magnesium values as magnesium oxide, which is recycled to the process, and the volatile materials are absorbed in water, thereby providing a highly efficient and relatively non-polluting system for purifying TNT.

The process of the present invention comprises agitating crude TNT containing unsymmetrical TNT isomers with an aqueous solution consisting essentially of a mixture of magnesium sulfite and magnesium bisulfite at temperatures above or below the melting point of the crude TNT, e.g. from about 20° to 100° C, particularly between 80° and 100° C. During the process the magnesium sulfite-bisulfite mixture reacts with the reactive meta nitro groups, thereby converting the unsymmetrical isomers into magnesium 2,4-dinitrotoluene-3-and-5-sulfonates, which are soluble in the aqueous solution and thus can be separated from the insoluble, purified TNT. When solid crude TNT is employed in the process, it is desirable to utilize the TNT in finely divided form and advantageously to carry out the process in an apparatus, such as a ball mill, containing grinding and/or attrition elements, which continuously comminute the TNT particles and/or expose fresh surfaces thereof to the aqueous sulfite solution and thereby optimize the purification reaction.

Normal magnesium sulfite is not sufficiently soluble in water to provide a significant purification action on crude TNT. However, by introducing sufficient sulfur dioxide into a mixture of water and normal magnesium sulfite or magnesium hydroxide, the pH of the aqueous mixture can be reduced to the 7 to 8 range, thereby forming a water-soluble mixture of magnesium sulfite and magnesium bisulfite, which is an effective and powerful agent for purifying crude TNT. During the purification reaction the pH of the aqueous magnesium sulfite-bisulfite solution rises substantially. For example, as shown in example 1 below, the pH of the solution rises from pH 7.1 initially to pH 8.9 at the conclusion of the purification reaction. In large scale operations it may be desirable to control the pH of the liquor e.g. between 7 and 8 by adding sulfur dioxide during the purification reaction to maintain optimum conditions. However, if the initial pH of the reaction mixture is too low, the mixture becomes acid during the reaction with the result that a satisfactory purification of the TNT is not obtained. For example, it was found that when the initial pH of the reaction mixture (obtained by mixing the crude TNT with the aqueous magnesium sulfite-bisulfite mixture produced from sulfur dioxide and magnesium hydroxide) was 6.3, the pH declined during the reaction to 2.1, whereby an unsatisfactory (insufficient) purification of the crude TNT was obtained. It is believed that for good results the aqueous magnesium sulfite-bisulfite solution should be maintained essentially at a pH of at least about 6.8 during the purification reaction.

The amount of magnesium sulfite-bisulfite employed depends mainly on the amount of unsymmetrical TNT isomers present in the crude TNT and the degree of purification desired, and to a lesser extent on other factors, such as the concentration of the sulfite solution and time and temperature of the reaction. Generally, the magnesium sulfite-bisulfite mixture is employed in an amount not substantially exceeding that required to react with and remove the unsymmetrical TNT isomers so as to minimize the reaction thereof with α TNT and consequent loss of yield of purified TNT. The quantity of water in the aqueous sulfite reaction liquor can be varied widely as long as a readily agitated reaction mixture is obtained.

The TNT to be purified according to the present process is preferably washed with water and/or aqueous alkaline solution to remove small amounts of acid, notably sulfuric and nitric acids, usually adhering thereto during manufacture. If crude TNT containing small amounts of such adhering acid is utilized as starting material, the acid can be neutralized by the magnesium hydroxide or magnesium sulfite employed, thereby forming a mixture of magnesium sulfite and magnesium bisulfite suitable for use in the present process.

The following examples illustrate specific embodiments of the method of carrying out the process of the present invention.

The crude TNT employed in the following examples was obtained from the Radford Army Ammunition Plant, in Radford, Vir. Prior to its use in the examples, it was subjected to a series of melt-washes with water at 80°–82° C until the washes were of neutral pH. The crude TNT washed in this manner had the following content of unsymmetrical TNT isomers (determined by gas chromatography) shown in Table I. The Table also shows a total of 0.123% of unsymmetrical TNT isomers of a typical Radford finished TNT product obtained by standard sellite purification.

TABLE I

| Isomeric TNT | Crude TNT % | Radford Finished TNT % |
|---|---|---|
| 2,3,5, | 0.159 | 0 |
| 2,4,5 | 2.61 | 0.042 |
| 2,3,4 | 1.48 | 0.081 |
| TOTAL | 4.25 | 0.123 |

EXAMPLE 1

An aqueous solution of magnesium sulfite-bisulfite having a pH 7.1 was prepared by mixing 0.9 gram magnesium oxide, 61 ml. water and 28 ml. aqueous sulfur dioxide containing 6% by weight of $SO_2$. The solution thus obtained was mixed with 60 grams of crude, molten TNT, and the mixture was agitated in an open vessel at 82° C for 15 minutes. The mixture was then cooled and the aqueous layer ("red water"), which had a pH 8.9, was decanted from the solidified TNT. The TNT thus obtained was melt-washed by agitating it with about 300 grams of hot (85° C) water acidified to pH 3 with sulfuric acid, cooling and separating the solidified TNT from the wash liquor, then melt-washed with about 300 grams water and finally melt-dried in vacuo. The purified TNT thus obtained had a setting point of 80.53° C (U.S. Military Specifications require a minimum setting point of 80.20° C for type I military explosive-grade TNT) and weighed 56.7 grams, corresponding to a yield of 94.5%.

In the foregoing example the amount of magnesium sulfite-bisulfite solution employed corresponded to 1.5 grams of MgO per 100 grams of crude TNT containing approximately 4% unsymmetrical isomers. When the example was repeated using an amount of the magnesium sulfite-bisulfite solution equivalent to 1 gram MgO per 100 grams of the crude TNT, the purified TNT obtained had a setting point of slightly below 80.20° C. Accordingly it appears that an amount of magnesium sulfite-bisulfite solution corresponding to a minimum of between 1 and 1.5 grams MgO per 100 grams of crude TNT containing approximately 4% unsymmetrical isomers (equivalent to between 1.4 and 2.1 mols of MgO per mol of unsymmetrical TNT isomers present in the crude TNT) is required to produce a purified TNT product having a setting point of at least 80.20° C required by U.S. Military Specifications.

EXAMPLE 2

20 grams of crude TNT were added to an aqueous solution of magnesium sulfite-bisulfite obtained by mixing 0.6 gram magnesium hydroxide, 15 ml. water and 18 ml. 6% aqueous sulfur dioxide. The mixture was heated to 95° C for 30 minutes with agitation to obtain thorough mixing of the two phases. The reaction mixture was cooled and the aqueous layer ("red water") was decanted from the solidified TNT. The TNT was melt-washed first with 1% sulfuric acid to remove magnesium impurities and then with water and finally air-dried. The purified TNT thus obtained weighed 19.2 grams, corresponding to a yield of 96%. Analysis of the purified TNT by gas-liquid chromatography showed that it contained 0.06% unsymmetrical TNT isomers and 99.87% of the 2,4,6-TNT isomer.

EXAMPLE 3

An aqueous solution of magnesium sulfite-bisulfite was prepared by agitating a mixture of 0.9 gram MgO, 27 ml. 6% aqueous $SO_2$ and 61 ml. water for 10 minutes. 60 grams of crude TNT were added and the mixture was heated to 80° C and agitated at that temperature for 30 minutes. The reaction mixture had a pH 7.2 10 minutes after start of the heating period and a pH 9.6 at the conclusion. The mixture was then processed in the manner described in Example 1 to recover the purified TNT. The purified TNT thus obtained had a setting point of 80.27° C and weighed 56.0 grams, corresponding to a yield of 93.3%

An important advantageous feature of the process of the present invention is the fact that the magnesium values in the water treatment liquors can be readily recovered as magnesium oxide and recycled to the process. This was demonstrated in Example 1 as follows. The spent sulfite liquor ("red water") separated from the purified TNT was combined with the acid wash layer and the resulting mixture (pH 8.3) was neutralized to pH 7.2 with sulfuric acid and evaporated to dryness, yielding 5.9 grams of solids. A 2.0 gram aliquot portion of the solids was heated to redness (about 600° C) in a crucible, yielding 0.4 gram of gray ash, which was found by analysis to consist of approximately 55% MgO and 45% $MgSO_4$. Complete conversion to MgO was accomplished by heating the ash to a still higher temperature in known manner. The MgO thus obtained, alone or as a mixture with the $MgSO_4$, can be recycled by mixing it with fresh MgO or $Mg(OH)_2$, as required, water and sufficient sulfur dioxide to form the magnesium sulfite-bisulfite solution for use in purifying crude TNT according to the process of the present invention. Volatile substances formed during the ignition of the solids from the spent sulfite liquor and consisting essentially of $SO_3$, $SO_2$, $CO_2$, nitrogen oxides and water, were recovered by absorption in water.

If desired, the solids recovered by calcination of the waste sulfite liquors obtained from the novel magnesium sulfite-bisulfite process can be separated into organic and inorganic constituents as follows. A 5.0 grams sample of the solids was agitated with 50 ml. dimethyl formamide at 100° C for 30 minutes. The resulting suspension was filtered and the filter cake was dried, yielding 1.0 gram of solids comprising approximately 90% MgSO$_4$ and 10% MgO. The filtrate was distilled in vacuo to remove the solvent, yielding 4.0 grams of a brown solid, which was shown by infrared spectral analysis to comprise a mixture of magnesium dinitrotoluene sulfonates. By heating the brown solid in an open crucible to about 600° C, a gray ash, consisting of a mixture of MgO and MgSO$_4$, mostly the former, was obtained.

It is surprising and obviously advantageous that the spent magnesium sulfite-bisulfite reaction liquor containing the magnesium salts of dinitrotoluene sulfonic acids formed in the present reaction, can be converted to a mixture of MgO and MgSO$_4$ consisting mostly of MgO by heating to a temperature of only 600° C, since a much higher temperature (over 1200° C) is required for the calcination of spent magnesium sulfite liquor obtained in paper manufacture to recover the magnesium values as a mixture of MgO and MgSO$_4$ consisting mostly of MgO.

In contrast, when conventional sodium sulfite (sellite) is employed to purify the crude TNT, the recovery of sodium values other than as NaSO$_4$ from the spent purification liquor is difficult and comparatively complicated.

The foregoing disclosure is merely illustrative of the principles of this invention and is not to be interpreted in a limiting sense. I wish it to be understood that I do not desire to be limited to the exact details of construction shown and described, because obvious modifications will occur to a person skilled in the art.

What is claimed is:

1. A process for purifying 2,4,6-trinitrotoluene containing unsymmetrical trinitrotoluene impurities, which comprises reacting the impure 2,4,6-trinitrotoluene with an aqueous medium consisting essentially of a mixture of magnesium sulfite and magnesium bisulfite to convert said isomeric impurities into products soluble in said aqueous medium, and separating the purified 2,4,6-trinitrotoluene from the aqueous medium containing said soluble conversion products.

2. The process of claim 1, wherein the aqueous magnesium sulfite-bisulfite reaction medium has a minimum pH of about 6.8.

3. The process of claim 1, wherein the aqueous magnesium sulfite-bisulfite medium is obtained by reaction of sulfur dioxide and magnesium oxide or hydroxide in aqueous medium.

4. The process of claim 1, wherein the amount of magnesium sulfite-bisulfite mixture corresponds to a minimum of about 1.4 mols magnesium oxide per mol of unsymmetrical isomers present in the impure trinitrotoluene.

5. The process of claim 1, wherein the reaction is carried out at a temperature sufficient to maintain the trinitrotoluene in molten condition.

6. The process of claim 1, wherein the magnesium sulfite-bisulfite reaction medium is maintained at a pH between about 7 and 8 during the reaction by addition of sulfur dioxide.

7. The process of claim 1, wherein the spent magnesium sulfite-bisulfite reaction liquor is calcined to recover the magnesium values largely as magnesium oxide, and the magnesium oxide thus obtained is recycled.

* * * * *